(12) United States Patent
Funaya

(10) Patent No.: US 11,759,181 B2
(45) Date of Patent: Sep. 19, 2023

(54) MEDICAL IMAGE CAPTURE APPARATUS FOR SHARING SETTING INFORMATION, PROGRAM FOR CONTROLLING THE SAME, AND SYSTEM

(71) Applicant: General Electric Company, Schenectady, NY (US)

(72) Inventor: Seiji Funaya, Tokyo (JP)

(73) Assignee: General Electric Company, Schenectady, NY (US)

( * ) Notice: Subject to any disclaimer, the term of this patent is extended or adjusted under 35 U.S.C. 154(b) by 303 days.

(21) Appl. No.: 17/154,656

(22) Filed: Jan. 21, 2021

(65) Prior Publication Data
US 2021/0236096 A1    Aug. 5, 2021

(30) Foreign Application Priority Data
Jan. 31, 2020   (JP) ................................ 2020-015135

(51) Int. Cl.
*A61B 8/08*     (2006.01)
*A61B 8/00*     (2006.01)
*G16H 30/40*    (2018.01)

(52) U.S. Cl.
CPC ............ *A61B 8/5215* (2013.01); *A61B 8/565* (2013.01); *G16H 30/40* (2018.01)

(58) Field of Classification Search
CPC ......... A61B 8/5215; A61B 8/565; A61B 8/44; A61B 8/4444; A61B 8/467; G16H 30/40
See application file for complete search history.

(56) References Cited

U.S. PATENT DOCUMENTS

2007/0058784 A1* 3/2007 Toshimitsu .............. A61B 6/00
378/162
2013/0111353 A1* 5/2013 Ueda ................... G06F 3/04817
709/219

FOREIGN PATENT DOCUMENTS

JP             6554579 B1      7/2019

\* cited by examiner

*Primary Examiner* — Colin T. Sakamoto
*Assistant Examiner* — Andrew W Begeman

(57) ABSTRACT

To provide a simpler implementation in which setting information is shared among a plurality of medical image capture apparatuses while maintaining intrinsic information each of the apparatuses has, in first memory in a first ultrasonic diagnostic apparatus UL1 are stored first data including first setting information set in the ultrasonic diagnostic apparatus UL1, and backup data for first intrinsic information included in the first data; in second memory in a second ultrasonic diagnostic apparatus UL2 is stored second data including second setting information set in the second ultrasonic diagnostic apparatus UL2; and once the second data is input via a network, a first processor rewrites the first data stored in the first memory into the second data, reads the first intrinsic information in the backup data, and rewrites the second intrinsic information into which the first intrinsic information has been rewritten, into the first intrinsic information in the backup data.

16 Claims, 13 Drawing Sheets

MEDICAL IMAGE CAPTURE APPARATUS FOR SHARING SETTING INFORMATION, PROGRAM FOR CONTROLLING THE SAME, AND SYSTEM

CROSS-REFERENCE TO RELATED APPLICATIONS

This application claims priority pursuant to 35 U.S.C. 119(a) of Japanese Application No. 2020-015135, filed Jan. 31, 2020, which application is incorporated herein by reference in its entirety.

FIELD OF THE INVENTION

The present invention relates to a medical image capture apparatus for capturing a medical image of an object to be imaged, a program for controlling the same, and a system having a plurality of medical image capture apparatuses connected with one another via a network.

BACKGROUND OF THE INVENTION

A medical image capture apparatus has a large number of preference settings. Contents of the preference settings, i.e., setting information, are in most cases customized according to the user's purpose and preferences. In a hospital having a plurality of ultrasonic diagnostic apparatuses, however, there is a need for sharing common setting information for the purpose of guaranteeing accuracy in examinations. Accordingly, for example, Japanese Patent No. 6554579 discloses a system in which common setting information is shared among a plurality of ultrasonic diagnostic apparatuses.

The setting information in a medical image capture apparatus also includes information intrinsic to the apparatus, such as, for example, an IP address, a serial number, user information, and the name of the department to which the apparatus belongs. Such intrinsic information is unsuitable for sharing among a plurality of medical image capture apparatuses. Therefore, there is a need for a simpler implementation in which setting information is shared among a plurality of medical image capture apparatuses while maintaining intrinsic information each of the apparatuses has.

BRIEF SUMMARY

This summary introduces concepts that are described in more detail in the detailed description. It should not be used to identify essential features of the claimed subject matter, nor to limit the scope of the claimed subject matter. The invention, in its one aspect made for solving the aforementioned problem is a medical image capture apparatus for capturing a medical image of an object to be imaged, said apparatus comprising memory and a processor, and being connected with another medical image capture apparatus via a network, wherein: in said memory are stored: first data including first setting information set in said medical image capture apparatus, said first setting information including first intrinsic information intrinsic to said medical image capture apparatus, and first shared information shared with said other medical image capture apparatus; and backup data for said first intrinsic information, in said other medical image capture apparatus is stored second data including second setting information set in said other medical image capture apparatus, said second setting information including: second intrinsic information intrinsic to said other medical image capture apparatus and different from said first intrinsic information; and second shared information shared with said first shared information, and once said second data is input via said network, said processor rewrites said first data stored in said memory into said second data, reads said first intrinsic information in said backup data, and rewrites said second intrinsic information into which said first intrinsic information has been rewritten, into said first intrinsic information in said backup data.

The invention, in another aspect, is a system comprising first and second medical image capture apparatuses for capturing medical images of objects to be imaged, said first and second medical image capture apparatuses being connected with each other via a network, wherein: said first medical image capture apparatus comprises first memory and a first processor, said second medical image capture apparatus comprises second memory and a second processor, in said first memory are stored: first data including first setting information set in said first medical image capture apparatus, said first setting information including first intrinsic information intrinsic to said first medical image capture apparatus, and first shared information shared with said second medical image capture apparatus; and backup data for said first intrinsic information, in said second memory is stored second data including second setting information set in said second medical image capture apparatus, said second setting information including: second intrinsic information intrinsic to said second medical image capture apparatus and different from said first intrinsic information; and second shared information shared with said medical image capture apparatus, said second processor outputs said second data to said network, and said first processor rewrites said first data stored in said first memory into said second data input via said network, reads said first intrinsic information in said backup data, and rewrites said second intrinsic information into which said first intrinsic information has been rewritten, into said first intrinsic information in said backup data.

According to the invention in the aspects above, once second data including second setting information in the aforementioned other medical image capture apparatus or second medical image capture apparatus is input to the aforementioned medical image capture apparatus or first medical image capture apparatus via a network, first data stored in the memory is rewritten into the second data. Then, second intrinsic information included in the rewritten second data is rewritten into the first intrinsic information in the backup data. Thus, after the second shared information is shared among a plurality of medical image capture apparatuses, the first intrinsic information can be maintained.

DETAILED DESCRIPTION

Embodiments of the present disclosure will now be described, by way of example, with reference to the Figures. The embodiments below address an ultrasonic diagnostic apparatus for capturing an ultrasonic image of an object to be imaged as an example of the medical image capture apparatus in the present invention.

Figure 1:
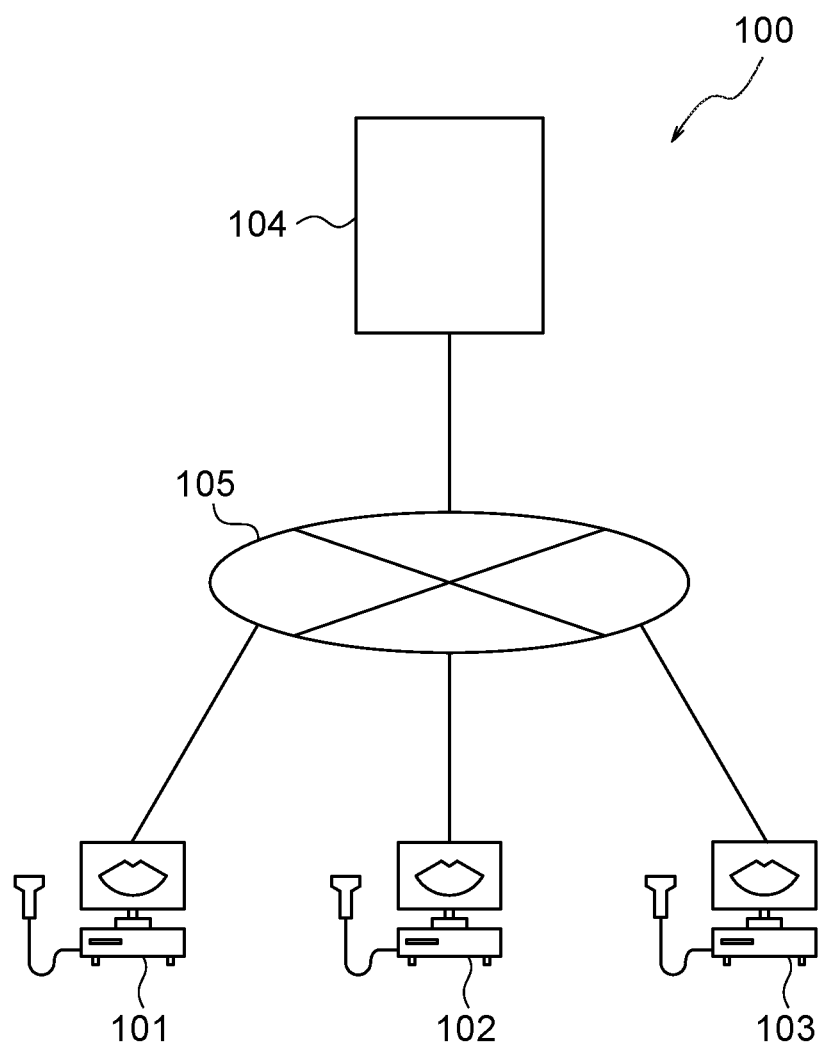
FIG. 1 is a diagram showing an outline of an overall configuration of a system in an embodiment of the present invention.

A system 100 shown in FIG. 1 comprises a plurality of ultrasonic diagnostic apparatuses 101, 102, 103, and a server 104. The plurality of ultrasonic diagnostic apparatuses 101, 102, 103 are connected with one another via a network 105. The plurality of ultrasonic diagnostic apparatuses 101, 102, 103 are also each connected with the server 104 via the network 105.

Figure 2:
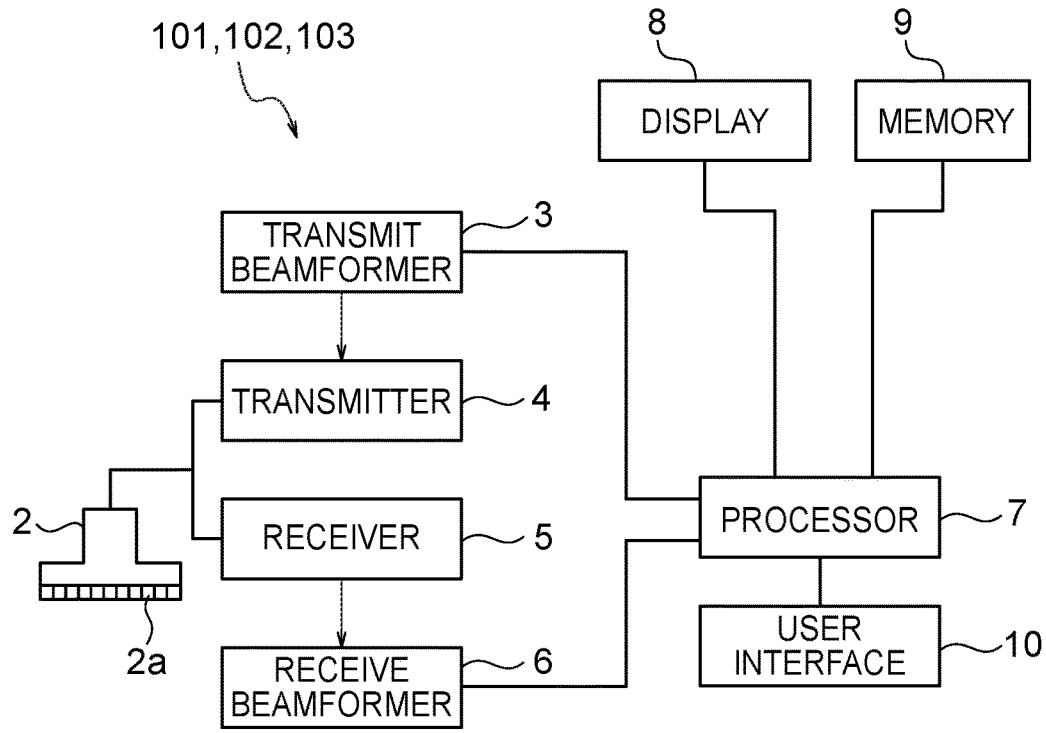
FIG. 2 is a block diagram showing a configuration of an ultrasonic diagnostic apparatus constituting the system shown in FIG. 1.

A configuration of each of the ultrasonic diagnostic apparatuses 101, 102, 103 is shown in FIG. 2. The ultrasonic diagnostic apparatuses 101, 102, 103 each comprise a transmit beamformer 3 and a transmitter 4 for driving a plurality of vibrator elements 2a arranged in an ultrasonic probe 2 to emit pulsed ultrasonic signals to a patient (not shown). The pulsed ultrasonic signals are reflected in the inside of the patient to generate echoes that return to the vibrator elements 2a. The echoes are converted into electrical signals by the vibrator elements 2a, and the electrical signals are received by a receiver 5. The electrical signals representing the received echoes, i.e., echo signals, undergo amplification, etc. with a required gain at the receiver 5, and then input to a receive beamformer 6, where receive beamforming is performed. The receive beamformer 6 outputs receive-beamformed ultrasound data.

The receive beamformer 6 may be a hardware beamformer or a software beamformer. In the case that the receive beamformer 6 is a software beamformer, it may comprise one or more processors including a graphics processing unit (GPU), a microprocessor, a central processing unit (CPU), a digital signal processor (DSP), or any one or more of other kinds of processors capable of executing logical operations. The processor(s) constituting the receive beamformer 6 may be constructed from a processor separate from a processor 7, which will be described later, or constructed from the processor 7.

The ultrasonic probe 2 may comprise electrical circuitry to perform all or part of the transmit and/or receive beamforming. For example, all or part of the transmit beamformer 3, transmitter 4, receiver 5, and receive beamformer 6 may be situated within the ultrasonic probe 2.

The ultrasonic diagnostic apparatuses 101, 102, 103 also each comprise the processor 7 for controlling the transmit beamformer 3, transmitter 4, receiver 5, and receive beamformer 6. The processor 7 is in electronic communication with the ultrasonic probe 2. The processor 7 may control the ultrasonic probe 2 to acquire ultrasound data. The processor 7 controls which of the vibrating elements 2a are active, and the shape of an ultrasonic beam transmitted from the ultrasonic probe 2. The processor 7 is also in electronic communication with the display 8, and the processor 7 may process the ultrasound data into ultrasonic images for display on the display 8. The phrase "electronic communication" may be defined to include both wired and wireless connections. The processor 7 may include a central processing unit (CPU) according to one embodiment. According to other embodiments, the processor 7 may include other electronic components capable of carrying out processing functions, such as a digital signal processor, a field-programmable gate array (FPGA), a graphics processing unit (GPU), or any other type of processor. According to other embodiments, the processor 7 may include a plurality of electronic components capable of carrying out processing functions. For example, the processor 7 may include two or more electronic components selected from a list of electronic components including: a central processing unit, a digital signal processor, a field-programmable gate array, and a graphics processing unit.

The processor 7 may also include a complex demodulator (not shown) that demodulates RF data. In another embodiment, the demodulation can be carried out earlier in the processing chain.

The processor 7 is adapted to perform one or more processing operations according to a plurality of selectable ultrasonic modalities on the data. The data may be processed in real-time during a scanning session as the echo signals are received. For the purpose of this disclosure, the term "real-time" is defined to include a procedure that is performed without any intentional delay.

The data may be temporarily stored in a buffer (not shown) during ultrasonic scanning, so that they can be processed in a live operation or in an off-line operation not in real-time. In this disclosure, the term "data" may be used in the present disclosure to refer to one or more datasets acquired with an ultrasonic apparatus.

The ultrasound data may be processed by other or different mode-related modules by the processor 7 (e.g., B-mode, color Doppler, M-mode, color M-mode, spectral Doppler, elastography, TVI, strain, strain rate, and the like) to form data for ultrasonic images. For example, one or more modules may produce ultrasonic images in B-mode, color Doppler, M-mode, color M-mode, spectral Doppler, elastography, TVI, strain, strain rate, and combinations thereof, and the like. The image beams and/or image frames are stored and timing information indicating a time at which the data was acquired in memory may be recorded. The modules may include, for example, a scan conversion module to perform scan conversion operations to convert the image frames from coordinate beam space to display space coordinates. A video processor module may be provided that reads the image frames from memory and displays the image frames in real-time while a procedure is being carried out on the patient. The video processor module may store the image frames in image memory, from which the ultrasonic images are read and displayed on the display 8.

The ultrasound data before the scan conversion operations will be referred to herein as raw data. The data after the scan conversion operations will be referred to herein as image data.

In the case that the processor 7 includes a plurality of processors, the aforementioned processing tasks to be handled by the processor 7 may be handled by the plurality of processors. For example, a first processor may be utilized to demodulate and decimate the RF signal while a second processor may be used to further process the data prior to displaying an image.

In the case that the receive beamformer 6 is a software beamformer, for example, its processing functions may be carried out by a single processor or by a plurality of processors.

The display 8 is an LCD (Liquid Crystal Display), an organic EL (Electro-Luminescence) display, or the like.

The memory 9 is any known data storage medium, and comprises non-transitory storage media and transitory storage media. The non-transitory storage media include, for example, a non-volatile storage medium such as an HDD (Hard Disk Drive) and ROM (Read Only Memory). The non-transitory storage media may include a portable storage medium such as a CD (Compact Disk), a DVD (Digital Versatile Disk), USB (Universal Serial Bus) memory, and HDD. Programs executed by the processor 7 are stored in a non-transitory storage medium.

The transitory storage medium is a volatile storage medium such as RAM (Random Access Memory).

Figure 3:
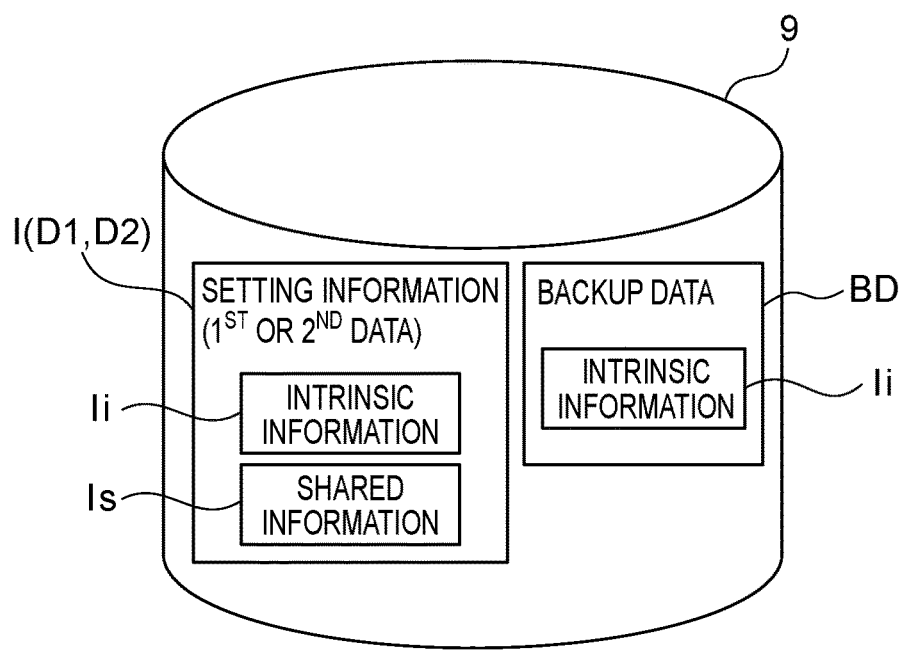
FIG. 3 is a diagram showing information stored in the memory of the ultrasonic diagnostic apparatus.

Setting information I set in each of the plurality of the ultrasonic diagnostic apparatuses 101, 102, 103 is stored in the memory 9. The setting information I includes a plurality of preference settings, which include intrinsic information Ii intrinsic to each of the ultrasonic diagnostic apparatuses 101, 102, 103, and shared information Is shared among the ultrasonic diagnostic apparatuses 101, 102, 103, as shown in FIG. 3. The intrinsic information Ii includes information on peripheral devices, such as, for example, a printer, connected to each of the ultrasonic diagnostic apparatuses 101, 102, 103, and an IP address, a serial number, information identifying an operator, and the like, for each of the ultrasonic diagnostic apparatuses 101, 102, 103. The intrinsic information Ii in the ultrasonic diagnostic apparatuses 101, 102, 103 has mutually different contents. The shared information Is includes, for example, imaging conditions for acquiring an ultrasonic image, reconstruction conditions for performing image reconstruction based on data of the ultrasonic image, and the like. Although the shared information Is in the ultrasonic diagnostic apparatuses 101, 102, 103 may sometimes have mutually different contents before sharing, it has the same contents after sharing.

The setting information I constitutes first or second data D1, D2, which will be discussed later. In addition to the first or second data D1, D2, the memory 9 stores therein backup data BD for the intrinsic information Ii. The first or second data D1, D2 and backup data BD may be stored in the same memory 9. In the case that each of the ultrasonic diagnostic apparatuses 101, 102, 103 has a plurality of units of memory 9, the first or second data D1, D2 and backup data BD may be stored in different units of memory.

The user interface 10 can accept an operator's input. For example, the user interface 10 accepts an input of a command and/or information from a user. The user interface 10 is adapted to include a keyboard, hard keys, a trackball, a rotary control, soft keys, and the like. The user interface 10 may include a touch screen that displays soft keys and the like.

For example, the user interface 10 may accept an operator's input of the setting information I. However, not all the setting information I may be input at the user interface 10, and the setting information I may be stored in the memory 9 from a portable storage medium, for example.

As will be discussed later, at least one of the ultrasonic diagnostic apparatuses 101, 102, 103 outputs the setting information I to the network 105. The one of the ultrasonic diagnostic apparatuses 101, 102, 103 that outputs the setting information I to the network 105 will be referred to herein as second ultrasonic diagnostic apparatus UL2. The setting information I (the second data D2 described later) output to the network 105 is input to the server 104, from which it is input to the ultrasonic diagnostic apparatuses 101, 102, 103 via the network 104. One or more of the ultrasonic diagnostic apparatuses 101, 102, 103 different from the second ultrasonic diagnostic apparatus UL2, that is, an apparatus(es) different from the apparatus from which the setting information I input from the server 104 was output will be referred to herein as first ultrasonic diagnostic apparatus UL1. The first ultrasonic diagnostic apparatus UL1 and second ultrasonic diagnostic apparatus UL2 are distinguished for the purpose of explanation, so that any one of the ultrasonic diagnostic apparatuses 101, 102, 103 may be the first ultrasonic diagnostic apparatus UL1 or the second ultrasonic diagnostic apparatus UL2. The first ultrasonic diagnostic apparatus UL1 is an exemplary embodiment of the medical image capture apparatus in accordance with the present invention. The second ultrasonic diagnostic apparatus UL2 is an exemplary embodiment of the other ultrasonic diagnostic apparatus in the present invention.

Figure 4:
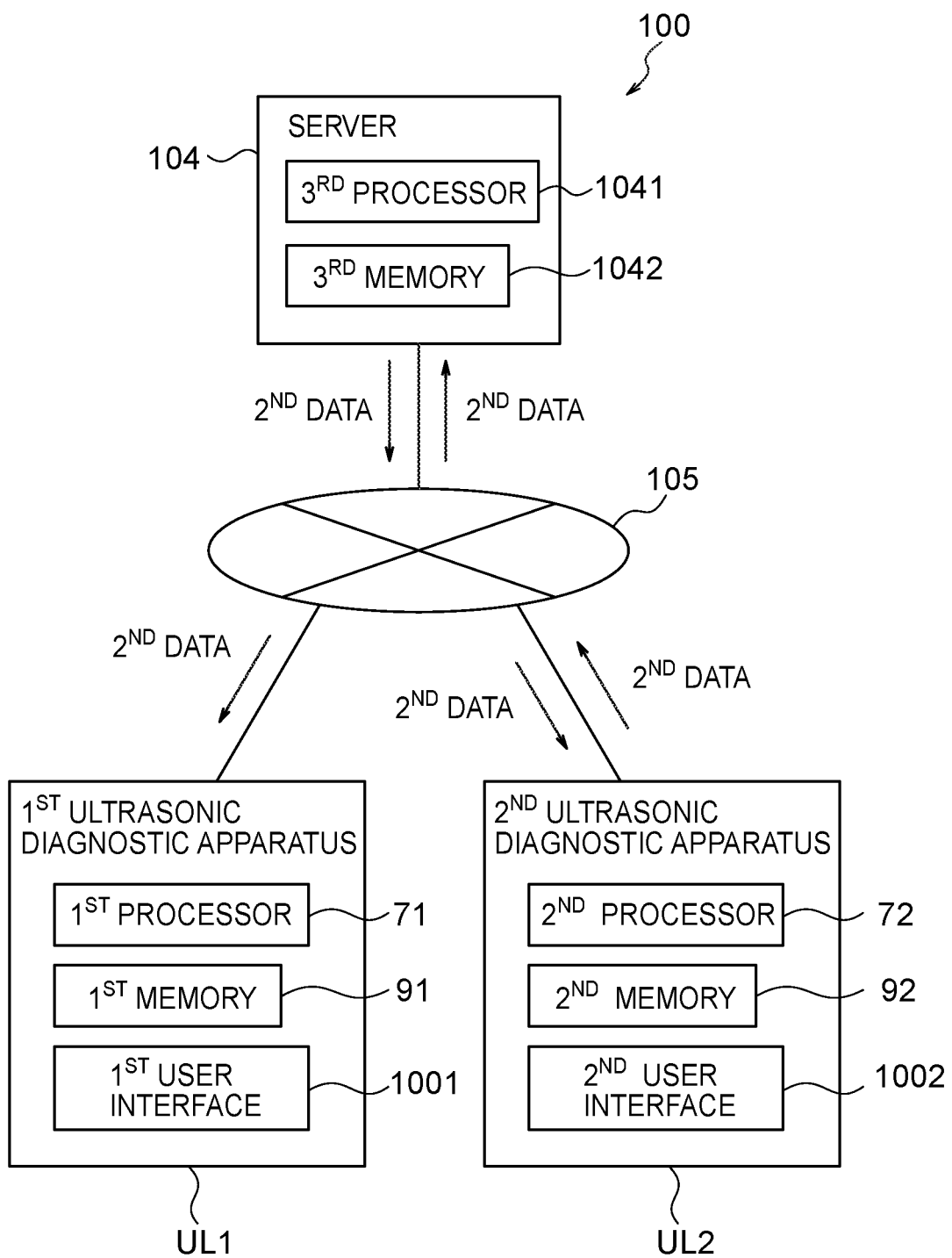
FIG. 4 is a block diagram showing a first ultrasonic diagnostic apparatus, a second ultrasonic diagnostic apparatus, and a server in the system of the embodiment.

The processor 7, memory 9, and user interface 10 in the first ultrasonic diagnostic apparatus UL1 are designated as a first processor 71, first memory 91, and a first user interface 1001, as shown in FIG. 4. The processor 7, memory 9, and user interface 10 in the second ultrasonic diagnostic apparatus UL2 are designated as a second processor 72, second memory 92, and a second user interface 1002, as shown in FIG. 4.

Figure 9:
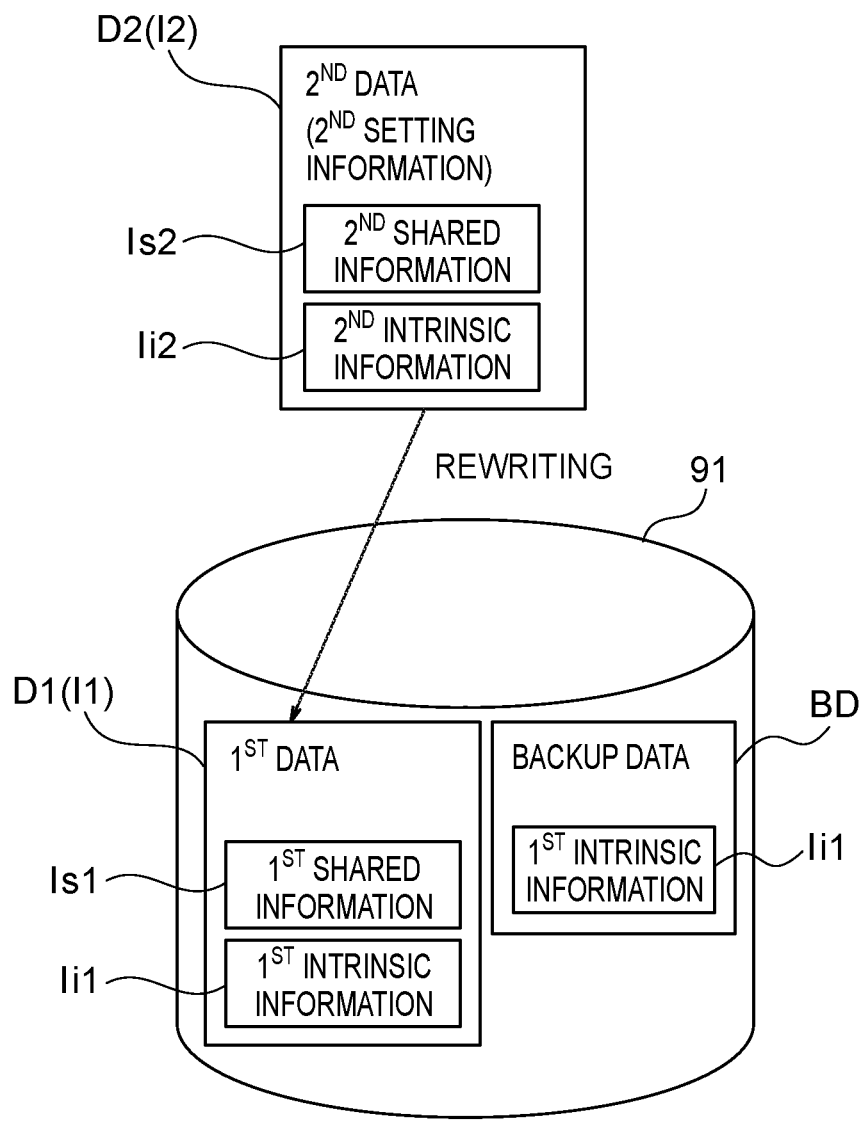
FIG. 9 is a diagram explaining rewriting of first data stored in first memory into second data.
Figure 10:
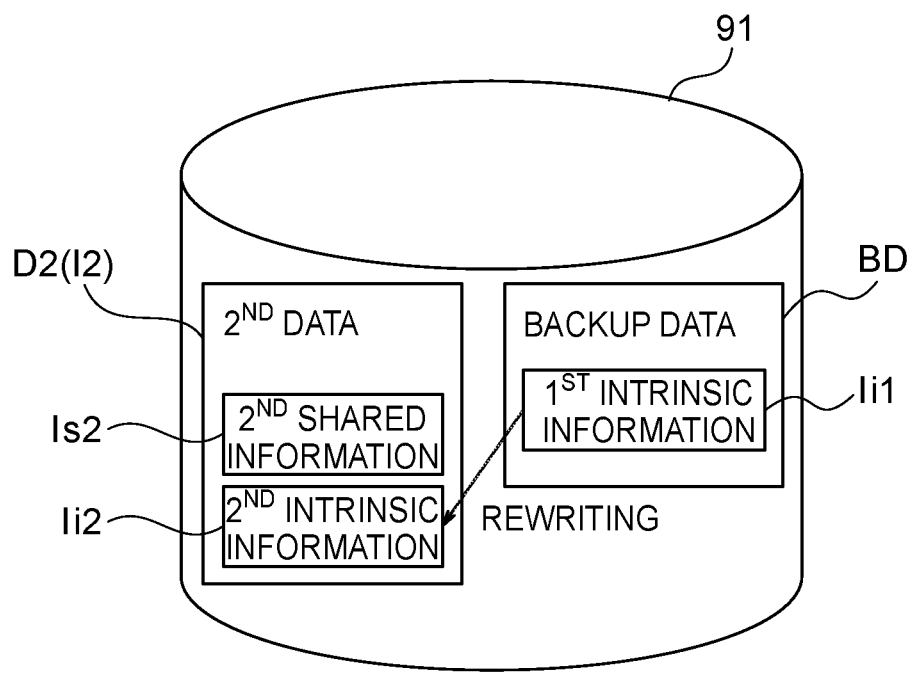
FIG. 10 is a diagram explaining rewriting of second intrinsic information into first intrinsic information in backup data.

In the first memory 91 is stored the first data D1 (see FIGS. 9 and 10). The first data D1 includes first setting information I1. The intrinsic information and shared information in the first setting information I1 will be referred to herein as first intrinsic information Ii1 and first shared information Is1, respectively. In the first memory 91 is also stored backup data BD for the first intrinsic information Ii1 (see FIGS. 9 and 10). The first setting information I1 may be input by the operator at the first user interface 1001.

Figure 6:
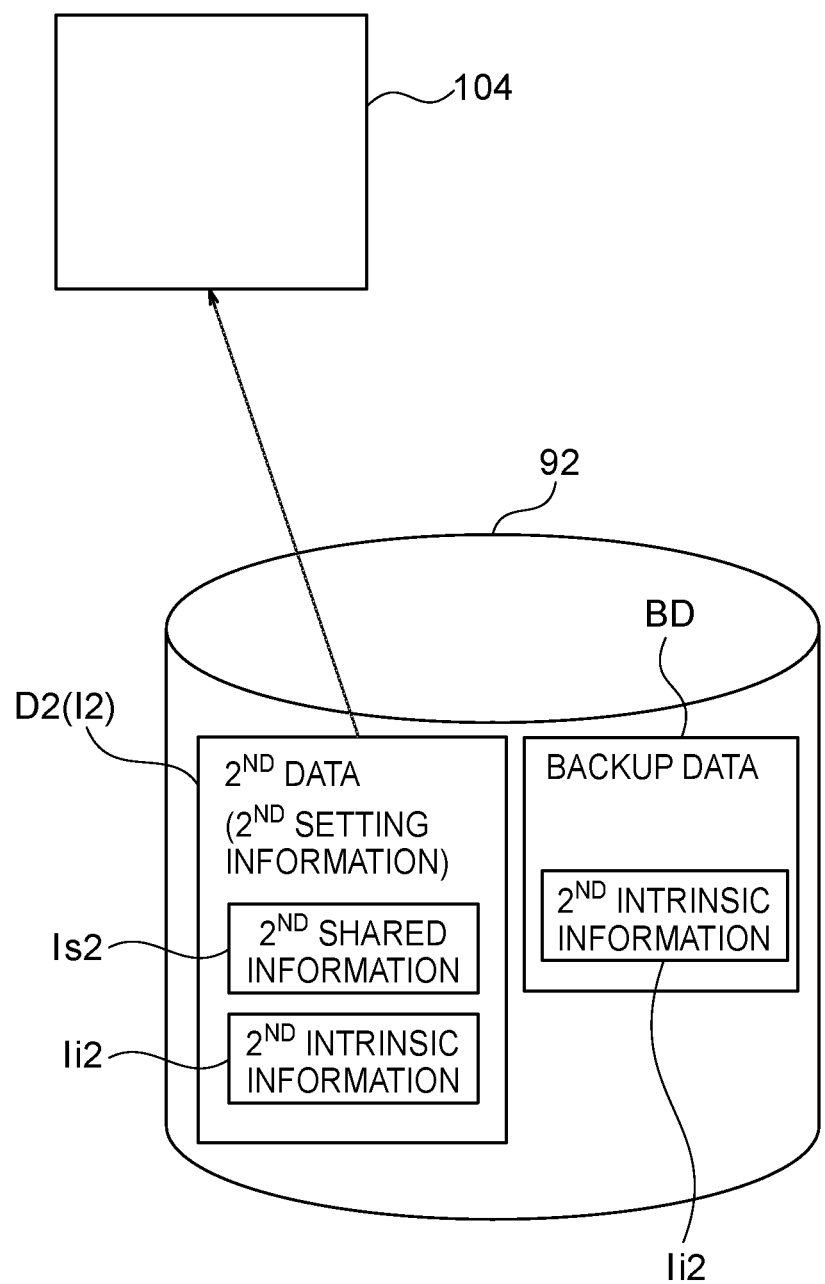
FIG. 6 is a diagram explaining sending of second data from the second ultrasonic diagnostic apparatus to the server.
Figure 7:
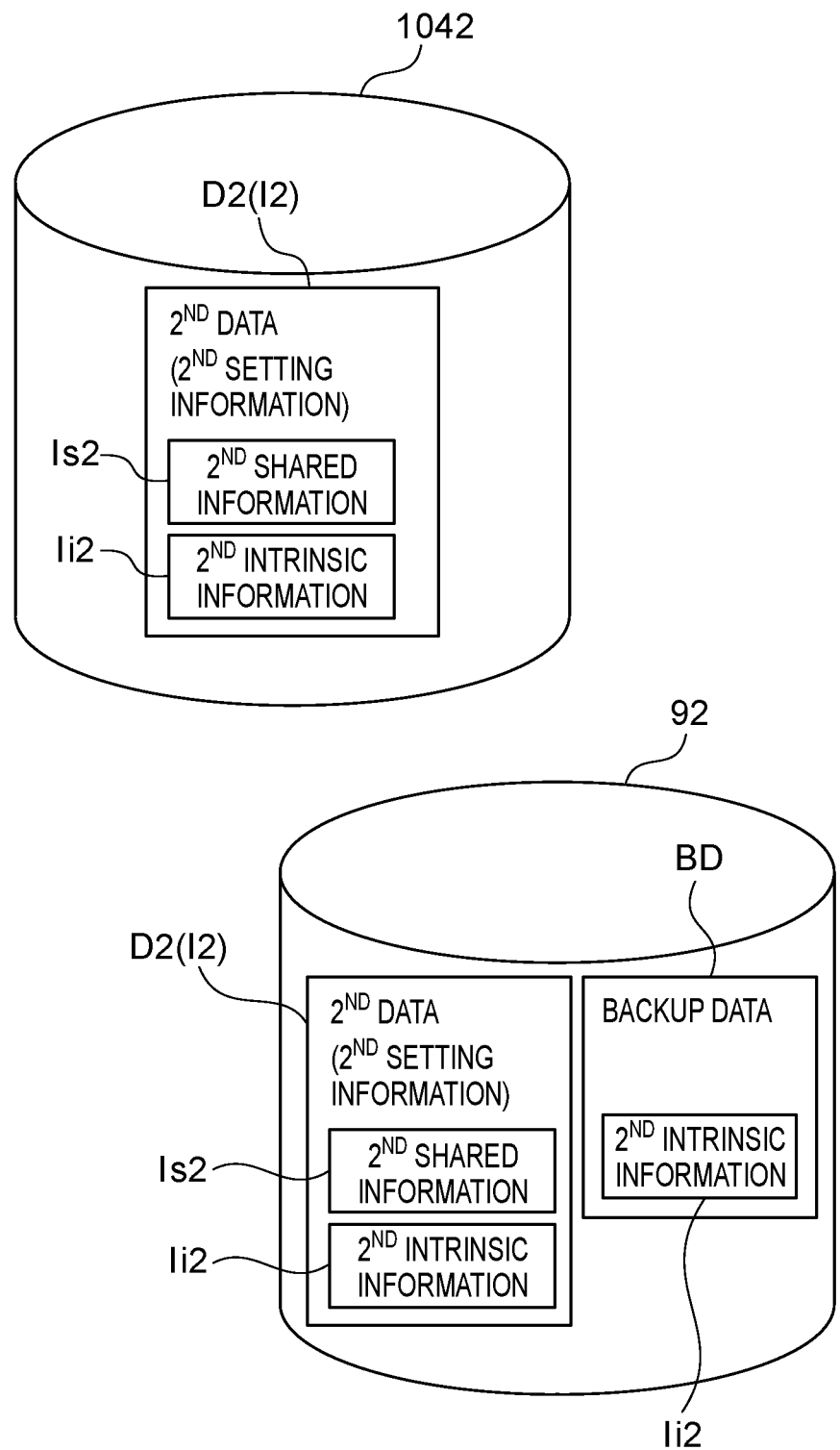
FIG. 7 is a diagram explaining storing of the second data input to the server into third memory.

In the second memory 92 is stored the second data D2 (see FIGS. 6 and 7). The second data D2 includes second setting information I2. The intrinsic information and shared information in the second setting information I2 will be referred to herein as second intrinsic information Ii2 and second shared information Is2, respectively. In the second memory 92 is also stored backup data BD for the second intrinsic information Ii2 (see FIGS. 6 and 7). The second setting information I2 may be input by the operator at the second user interface 1002.

The server 104 also has a third processor 1041 and third memory 1042, as shown in FIG. 4. The third processor 1041 and third memory 1041 are constructed from a processor and a storage medium that a publicly known server has.

Figure 5:
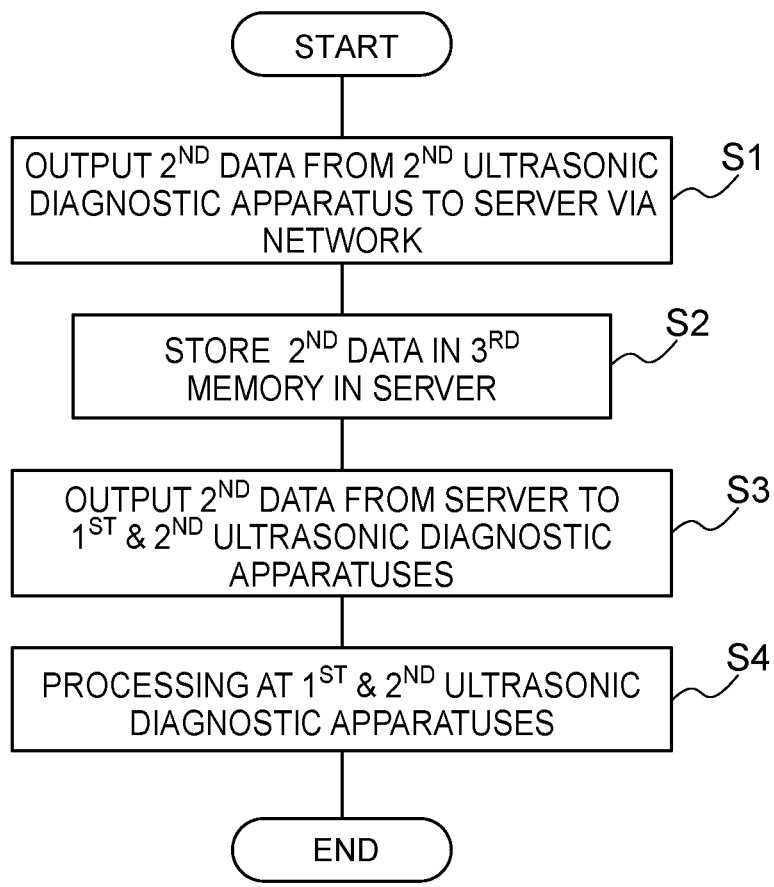
FIG. 5 is a flow chart showing an example of processing in the system of the embodiment.

Next, an operation of the system 100 in the present embodiment will be described hereinbelow. FIG. 5 is a flow chart showing processing in the system 100 in the present embodiment. It is assumed that before the processing of the flow charts in FIGS. 5 and 8, which will be described later, is started, contents in the first shared information Is1 are different from those in the second shared information Is2.

Referring to FIG. 5, first, at Step S1, the second processor 72 outputs the second data D2 stored in the second memory 92 as shown in FIG. 6 to the network 105 (not shown in FIG. 6), and sends it to the server 104. The second processor 72 appends, to the second data D2, identification information (not shown) for identifying the second ultrasonic diagnostic apparatus UL2 in which the second data D2 is stored, and outputs the resulting data to the server 104 via the network 105. The output second data D2 may comprise a single file or a plurality of files.

At Step S1, the second user interface 1002 may accept an input of the second setting information I2, and once the second setting information I2 has been stored in the second memory 92 as the second data D2, the second processor 72 may output the second data D2 to the network 105. The whole second setting information I2 included in the second data stored in the second memory 92 may be output to the server 104. Alternatively, as will be discussed later, in the case that the second data D2 has been already stored in the third memory 1042, and when an input for modifying the contents of the second setting information I2 in the second data D2 stored in the second memory 92 is received by the second user interface 1002, only the modified second setting information I2 may be output to the server 104.

The identification information for identifying the second ultrasonic diagnostic apparatus UL2 may be, for example, a serial number included in the second intrinsic information, or information other than the serial number.

Next, at Step S2, the third processor 1041 stores into the third memory 1042 the second data D2 input from the second ultrasonic diagnostic apparatus UL2 to the server 104, as shown in FIG. 7. The third processor 1041 also stores into the third memory the identification information (not shown in FIG. 7) identifying the second ultrasonic diagnostic apparatus UL2 in which the second data D2 is stored and from which the second data D2 is sent.

Thus, the second data D2 stored in the third memory 1042 at Step S2 can play a role as a backup of the second data D2 stored in the second ultrasonic diagnostic apparatus UL2. Therefore, the setting information I stored in the ultrasonic diagnostic apparatuses 101, 102, 103 is output to the server 104 via the network 105 and stored in the third memory 1042, whereby the server 104 can play a role to making a backup of the setting information I in the ultrasonic diagnostic apparatuses 101, 102, 103.

Next, at Step S3, the third processor 1041 outputs the second data D2 stored in the third memory 1042 to the first and second ultrasonic diagnostic apparatuses UL1, UL2 via the network 105, along with the identification information for the second ultrasonic diagnostic apparatus UL2, as shown in FIG. 4. The output second data D2 includes the second intrinsic information Ii2, in addition to the second shared information Is2. By thus outputting the second intrinsic information Ii2 not to be shared with the first ultrasonic diagnostic apparatus UL1 without being removed from the second data D2, can be eliminated the needs for the processing by the third processor 1041 analyzing the second setting information I2 included in the second data D2 to discriminate between shared information to be shared and intrinsic information not to be shared with the first ultrasonic diagnostic apparatus UL1, and for the processing by the third processor 1041 selectively outputting only shared information.

Next, at Step S4, processing at the first and second ultrasonic diagnostic apparatuses UL1, UL2 is performed.

Figure 8:
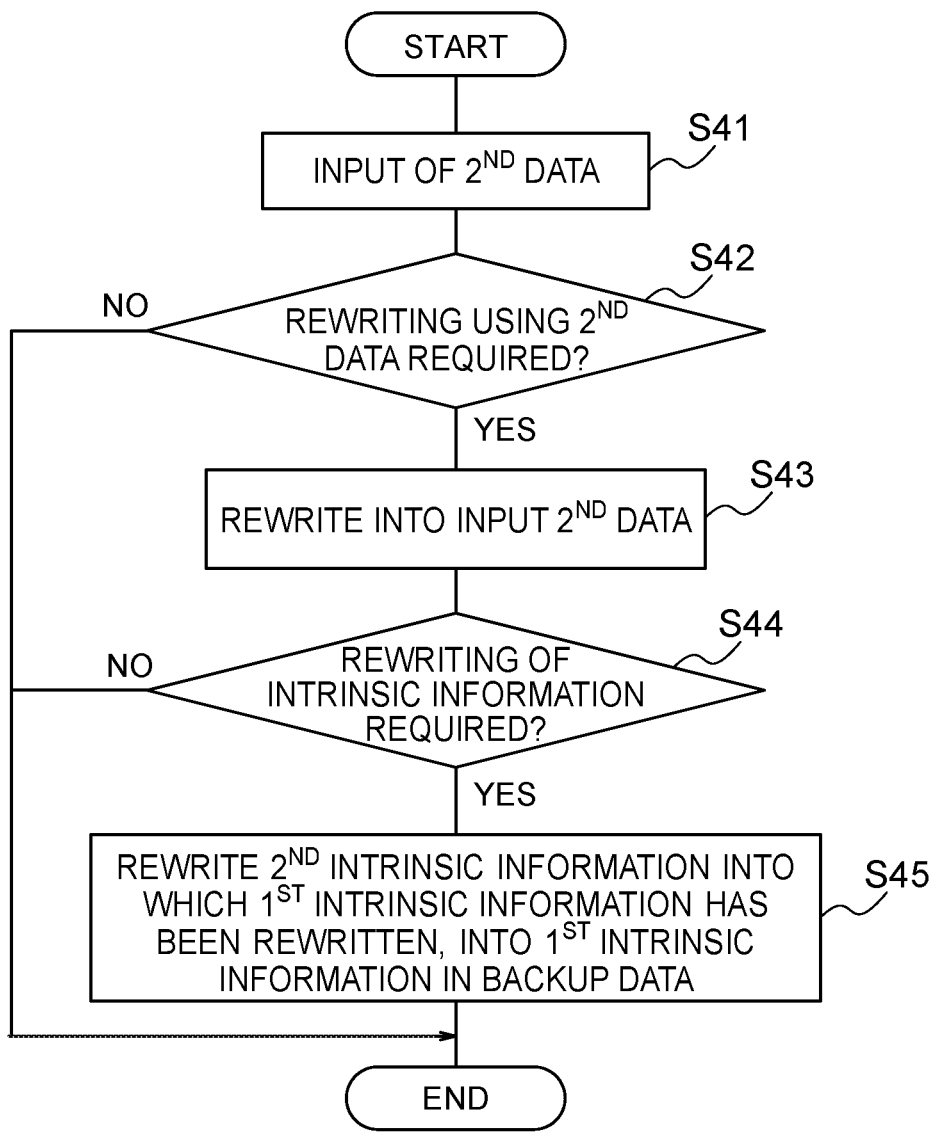
FIG. 8 is a flow chart showing an example of processing in the ultrasonic diagnostic apparatus.

The processing at Step S4 will now be specifically described based on the flow chart in FIG. 8. First, at Step S41, the second data D2 and identification information are input to the first and second ultrasonic diagnostic apparatuses UL1, UL2.

At Step S41, the first and second processors 71, 72 may display on a touch screen or the display 8 constituting the first and second user interfaces 1001, 1002 a screen for inquiring the operator whether or not to go to the processing at and after Step S42. In this case, when the operator selects to go to the processing at and after Step S42 on the displayed screen, the flow goes to the processing at and after Step S42.

Next, at Step S42, the first and second processors 71, 72 decide whether or not rewriting using the second data D2 input from the server 104 via the network 105 is necessary. For example, the first and second processors 71, 72 decide the need for rewriting by deciding whether or not the contents of the second setting information I2 included in the second data D2 input from the server 104 are the same as those of the first or second setting information I1, I2 stored in the first or second memory 91, 92 based on hash values or the like. The decision may be made on a file-by-file basis, for example.

In the case that the first and second processors 71, 72 have decided that the contents of the second setting information I2 included in the second data D2 input from the server 104 are not the same as those of the first or second setting information I1, I2 stored in the first or second memory 91, 92, they decide that there is the need to rewrite the first or second data D1, D2 stored in the first or second memory 91, 92 ("YES" at Step S42). On the other hand, in the case that the first and second processors 71, 72 have decided that the contents of the second setting information I2 included in the second data D2 input from the server 104 are the same as those of the first or second setting information I1, I2 stored in the first or second memory 91, 92, they decide that there is no need to rewrite the first or second data D1, D2 stored in the first or second memory 91, 92 ("NO" at Step S42).

When it is decided that there is no need for rewriting at Step S42, the processing is terminated. On the other hand, when it is decided that there is the need for rewriting at Step S42, the flow goes to the processing at Step S43. At Step S43, the first and second processors 71, 72 rewrite the first and second data D1, D2 stored in the first and second memory 91, 92 into the second data D2 input from the server 104. FIG. 9 shows the rewriting of the first data D1 into the second data D2 in the first memory 91.

Note that rewriting of the first and second data D1, D2 into the second data D2 means that the contents of the first and second setting information I1, I2 included in the first and second data D1, D2 in the first and second memory 91, 92 are rewritten into those of the second setting information I2 included in the second data D2 from the server 104. Therefore, for example, by rewriting from the contents of the first setting information I1 included in the first data D1 into those of the second setting information I2 included in the second data D2, the contents of the first shared information Is1, such as, for example, particulars of imaging conditions, in the first data D1 are rewritten into those of the second shared information Is2. Moreover, the contents of the first intrinsic information Ii1, such as the serial number, in the first data D1 are also rewritten into those of the second intrinsic information Ii2.

Note that the rewriting of the data may be performed only on the data for which it is decided that rewriting is needed at Step S42. For example, in the case that the need for rewriting is decided on a file-by-file basis, rewriting on a file-by-file basis may be performed.

Next, at Step S44, the first and second processors 71, 72 decide whether or not there is the need to further rewrite the rewritten second intrinsic information Ii2 stored in the first and second memory 91, 92. The first and second processors 71, 72 decide the need for rewriting of the second intrinsic information Ii2 referring to the identification information input from the server 104 along with the second data D2.

The first and second processors 71, 72 decide the need for rewriting of the second intrinsic information Ii2 by, for example, deciding whether or not the identification information input from the server 104 matches the first and second intrinsic information Ii1, Ii2 (the serial numbers, for example) in the backup data BD. The identification information input from the server 104 identifies the second ultrasonic diagnostic apparatus UL2. Therefore, the first processor 71 decides that the identification information input from the server 104 does not match the first intrinsic information Ii1 in the backup data BD, and decides that it is necessary to rewrite the second intrinsic information Ii2 ("YES" at Step S44).

On the other hand, the second processor 71 decides that the identification information input from the server 104 matches the second intrinsic information Ii2 in the backup data BD, and decides that it is unnecessary to rewrite the second intrinsic information Ii2 ("NO" at Step S44). In this case, the processing is terminated.

At Step S45, the first processor 71 rewrites the second intrinsic information Ii2, which has been rewritten from the first intrinsic information Ii1 at Step S43, into the first intrinsic information Ii1 in the backup data BD, as shown in FIG. 10. By the foregoing, the processing ends.

Note that rewriting from the second intrinsic information Ii2 into the first intrinsic information Ii1 means, again, that the contents of the second intrinsic information Ii2 are rewritten into those of the first intrinsic information Ii1. While the second data D2, second shared information Is2, and second intrinsic information Ii2 are shown in FIG. 10, they designate the contents of each of the second data D2, second shared information Is2, and second intrinsic information Ii2.

By completing the processing up to Step S45, the first ultrasonic diagnostic apparatus UL1 and second ultrasonic diagnostic apparatus UL2 can share the shared information having the same contents (those of the second shared information Is2). In addition to that, the first ultrasonic diagnostic apparatus UL1 can maintain the contents of the first intrinsic information Ii1. The contents of the first and second setting information I1, I2 may be displayed on the displays 8 in the first ultrasonic diagnostic apparatus UL1 and second ultrasonic diagnostic apparatus UL2.

Figure 11:
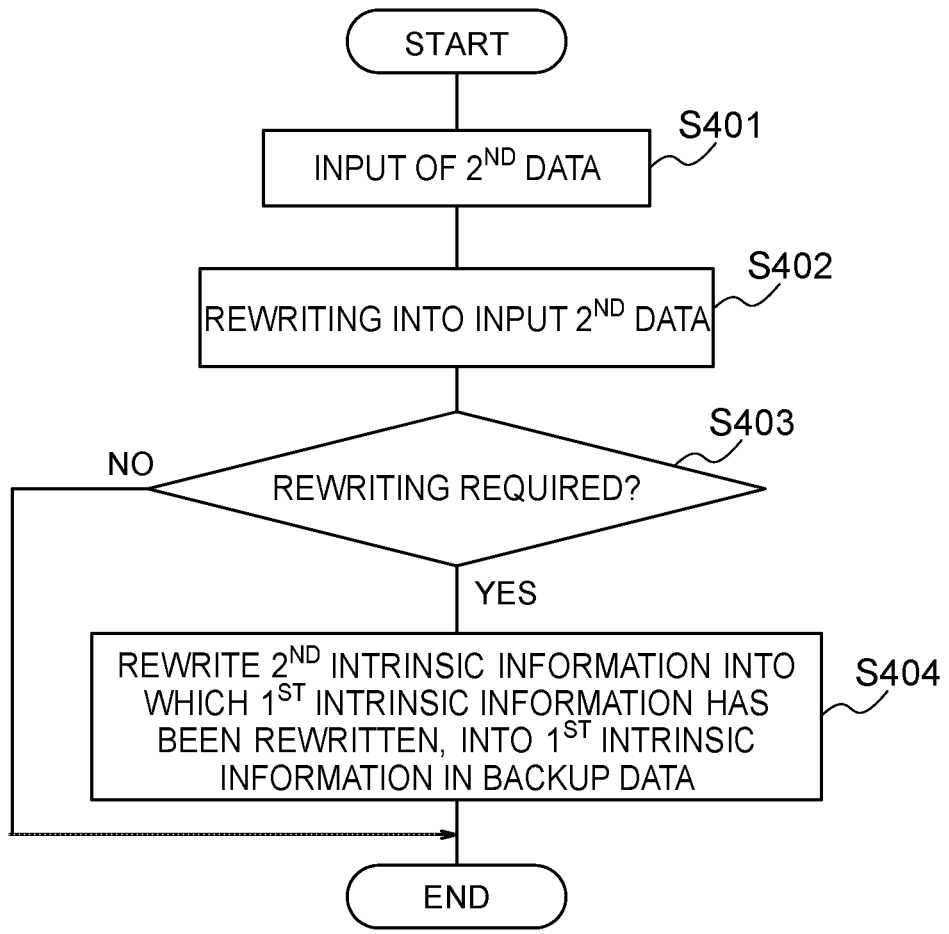
FIG. 11 is a flow chart showing an example of processing in a first variation.

Next, variations of the embodiment will be described hereinbelow. First, a first variation will be described. In the first variation, the processing at Step S4 is different, where rewriting into the second data D2 input from the server 104 is performed without making the decision at Step S42. FIG. 11 is a flow chart showing the processing at Step S4 of the first variation.

First, at Step S401, the same processing as that at Step S41 is performed. Next, at Step S402, the first processor 71 rewrites the first data D1 stored in the first memory 91 into the second data D2 input at Step S401, as in Step S43. Moreover, the second processor 72 rewrites the second data D2 stored in the second memory 9 into the second data D2 input at Step S401 to perform restoration.

Next, at Steps S403 and S404, the same processing as that at Steps S44 and S45 is performed.

Figure 12:
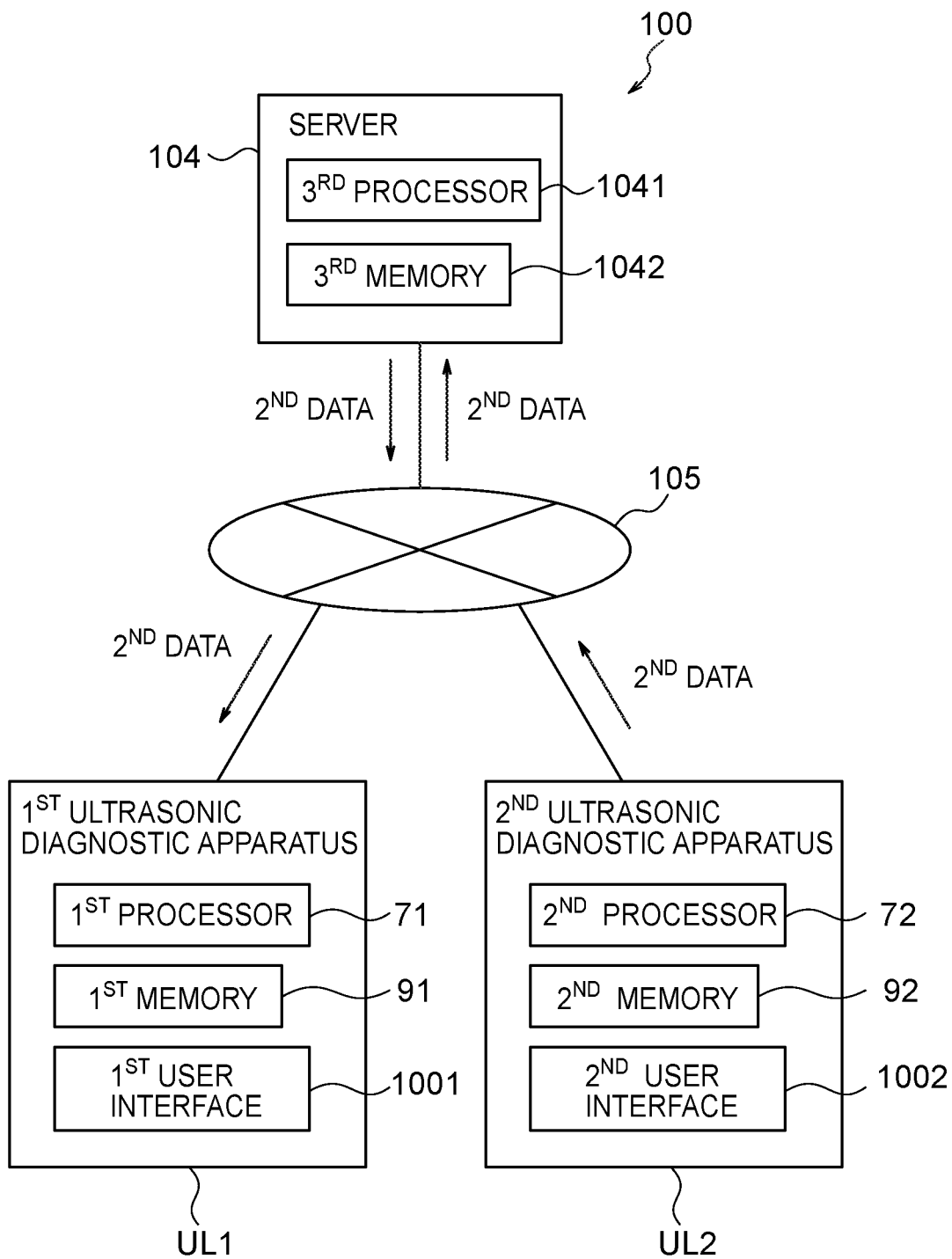
FIG. 12 is a block diagram showing the first ultrasonic diagnostic apparatus, second ultrasonic diagnostic apparatus, and server in the system of a second variation.

Next, a second variation will be described. In the system 100 in the second variation, the second data D2 from the server 104 is not input to the second ultrasonic diagnostic apparatus UL2, as shown in FIG. 12.

Figure 13:
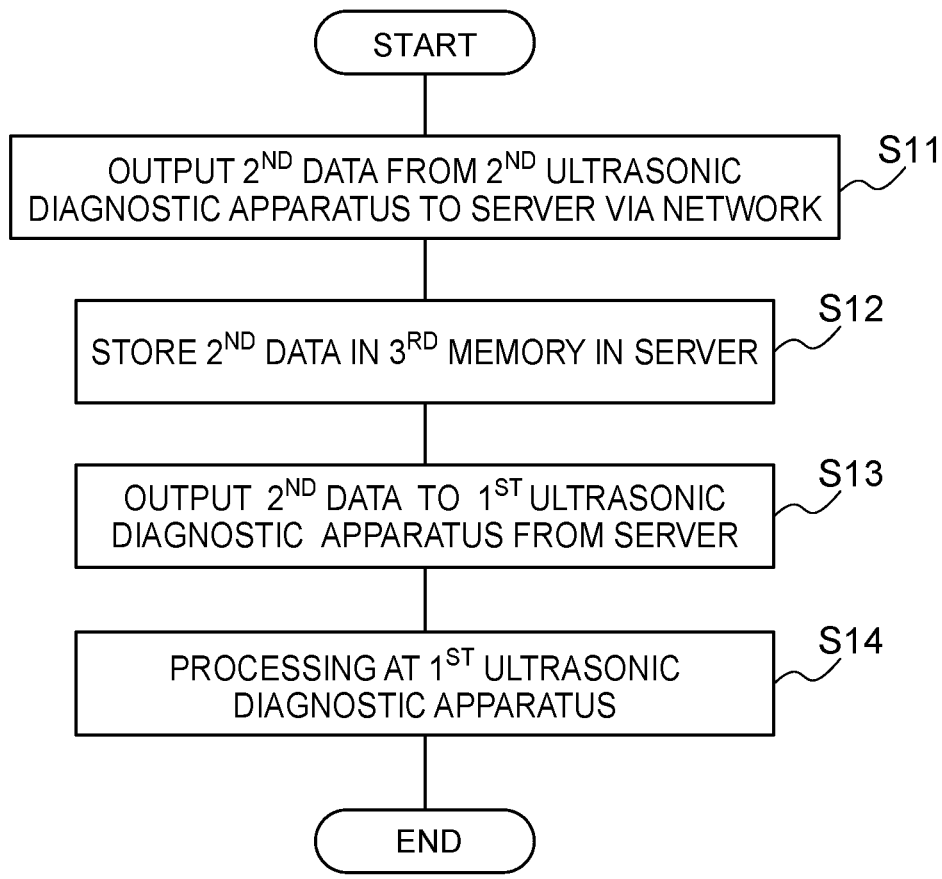
FIG. 13 is a flow chart showing an example of processing in the system of the second variation.

The processing will now be specifically described based on a flow chart in FIG. 13. The processing at Steps S11 and S12 is same as that at Steps S1 and S2 in FIG. 5. At Step S13, the third processor 1041 outputs the second data D2 stored in the third memory 1042 to the first ultrasonic diagnostic apparatus UL1 via the network 105. The third processor 1042 outputs the second data D2 to the first ultrasonic diagnostic apparatus UL1, except the second ultrasonic diagnostic apparatus UL2, referring to the identification information for identifying the second ultrasonic diagnostic apparatus UL2 in which the second data D2 sent to the server 104 is stored.

Figure 14:
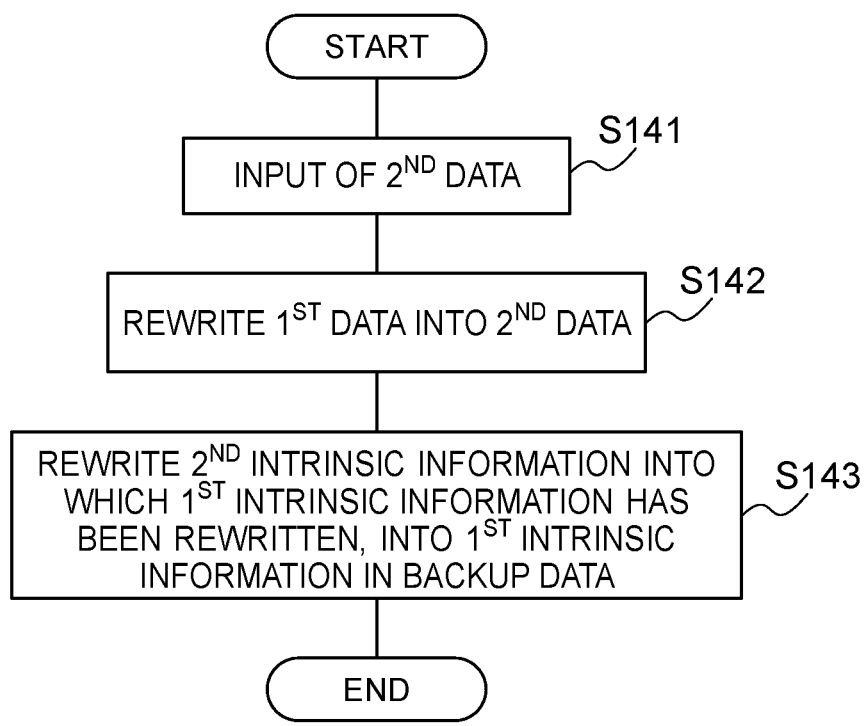
FIG. 14 is a flow chart showing an example of processing in the ultrasonic diagnostic apparatus of the second variation.

Next, at Step S14, processing at the first ultrasonic diagnostic apparatus UL1 is performed. The processing at Step S14 will be specifically described based on a flow chart in FIG. 14.

First, at Step S141, the second data D2 is input to the first ultrasonic diagnostic apparatus UL1. In the present embodiment, it is not necessary to input the identification information to the first ultrasonic diagnostic apparatus UL1. At Step S141, again, the first processor 71 may display on the touch screen or display 8 constituting the first user interface 1001 a screen for inquiring the operator whether or not to go to the processing at and after Step S142, as in Step S41.

At Step S142, the first processor 71 rewrites the first data D1 stored in the first memory 91 into the second data D2 input from the server 104, as in Steps S43 and S402. Then, at Step S143, the same processing as that at Step S45 is performed.

Embodiments of the present disclosure shown in the drawings and described above are example embodiments only and are not intended to limit the scope of the appended claims, including any equivalents as included within the scope of the claims. Various modifications are possible and will be readily apparent to the skilled person in the art. It is intended that any combination of non-mutually exclusive features described herein are within the scope of the present invention. That is, features of the described embodiments can be combined with any appropriate aspect described above and optional features of any one aspect can be combined with any other appropriate aspect. Similarly, features set forth in dependent claims can be combined with non-mutually exclusive features of other dependent claims, particularly where the dependent claims depend on the same independent claim. Single claim dependencies may have been used as practice in some jurisdictions require them, but this should not be taken to mean that the features in the dependent claims are mutually exclusive.

For example, while the embodiments above address an ultrasonic diagnostic apparatus as an example of the medical image capture apparatus, the medical image capture apparatus in the present invention is not limited to the ultrasonic diagnostic apparatus. For example, the present invention may be similarly applied to medical image capture apparatuses including X-ray CT apparatuses and MM apparatuses.

Moreover, the embodiment described above may be a method of controlling a medical image capture apparatus for capturing a medical image of an object to be imaged, said apparatus comprising memory and a processor, and being connected with another medical image capture apparatus via a network, wherein:

in said memory is stored said program for controlling, and in said memory are further stored: first data including first setting information set in said medical image capture apparatus, said first setting information including first intrinsic information intrinsic to said medical image capture apparatus, and first shared information shared with said other medical image capture apparatus; and backup data for said first intrinsic information, in said other medical image capture apparatus is stored second data including second setting information set in said other medical image capture apparatus, said second setting information including: second intrinsic information intrinsic to said other medical image capture apparatus and different from said first intrinsic information; and second shared information shared with said medical image capture apparatus, and said processor reads said program for controlling from said memory to:
 once said second data is input via said network, rewrite said first data stored in said memory into said second data,
 read said first intrinsic information in said backup data, and
 rewrite said second intrinsic information into which said first intrinsic information has been rewritten, into said first intrinsic information in said backup data.

Furthermore, the embodiment described above may be a method of controlling a system comprising first and second medical image capture apparatuses for capturing medical images of objects to be imaged, said first and second medical image capture apparatuses being connected to each other via a network, said first medical image capture apparatus comprising first memory and a first processor, said second medical image capture apparatus comprising second memory and a second processor, wherein:

in said first and second memory are stored programs for controlling by said first and second processors, in said first memory are further stored: first data including first setting information set in said first medical image capture apparatus, said first setting information including first intrinsic information intrinsic to said first medical image capture apparatus, and first shared information shared with said second medical image capture apparatus; and backup data for said first intrinsic information, in said second memory is further stored second data including second setting information set in said second medical image capture apparatus, said second setting information including: second intrinsic information intrinsic to said second medical image capture apparatus and different from said first intrinsic information; and second shared information shared with said first shared information, said second processor loads said program for controlling from said second memory to output said second data to said network, and said first processor loads said program for controlling from said second memory to:
 rewrite said first data stored in said memory into said second data input via said network,
 read said first intrinsic information in said backup data, and
 rewrite said second intrinsic information into which said first intrinsic information has been rewritten, into said first intrinsic information in said backup data.

The invention claimed is:

1. A medical image capture apparatus for capturing a medical image of an object to be imaged, said apparatus comprising memory and a processor, and being connected with another medical image capture apparatus via a network, wherein:
   in said memory are stored: first data including first setting information set in said medical image capture apparatus, said first setting information including first intrinsic information intrinsic to said medical image capture apparatus, and first shared information shared with said other medical image capture apparatus; and backup data for said first intrinsic information,
   in said other medical image capture apparatus is stored second data including second setting information set in said other medical image capture apparatus, said second setting information including: second intrinsic information intrinsic to said other medical image capture apparatus and different from said first intrinsic information; and second shared information shared with said medical image capture apparatus, and
   once said second data is input via said network, said processor
     rewrites said first data stored in said memory into said second data,
     reads said first intrinsic information in said backup data, and
     rewrites said second intrinsic information into which said first intrinsic information has been rewritten, into said first intrinsic information in said backup data.

2. The medical image capture apparatus as recited in claim 1, wherein:
   said apparatus is connected to a server via said network, said server being connected with said other medical image capture apparatus via said network, and
   said second data input via said network is data that is input from said other medical image capture apparatus to said server via said network and stored there.

3. A system comprising first and second medical image capture apparatuses for capturing medical images of objects to be imaged, said first and second medical image capture apparatuses being connected with each other via a network,
   said first medical image capture apparatus comprising first memory and a first processor,
   said second medical image capture apparatus comprising second memory and a second processor, wherein:
   in said first memory are stored: first data including first setting information set in said first medical image capture apparatus, said first setting information including first intrinsic information intrinsic to said first medical image capture apparatus, and first shared information shared with said second medical image capture apparatus; and backup data for said first intrinsic information,
   in said second memory is stored second data including second setting information set in said second medical image capture apparatus, said second setting information including: second intrinsic information intrinsic to said second medical image capture apparatus and different from said first intrinsic information; and second shared information shared with said first shared information,
   said second processor outputs said second data to said network, and
   said first processor
     rewrites said first data stored in said first memory into said second data input via said network,
     reads said first intrinsic information in said backup data, and rewrites said second intrinsic information into which said first intrinsic information has been rewritten, into said first intrinsic information in said backup data.

4. The system as recited in claim 3, comprising:
a server connected with said first and second medical image capture apparatuses via said network, wherein
said second processor outputs said second data to said server via said network,
said server outputs said second data to at least said first medical image capture apparatus via said network, and
said first processor performs rewriting of said first data using said second data input from said server.

5. The system as recited in claim 4, wherein:
said server comprises a third processor,
said third processor outputs said second data input into said server out to said first medical image capture apparatus via said network, and
said first processor performs rewriting said first data into said second data input from said server in a case that it decides that contents of said second setting information included in said second data input from said server are not identical to those of said first setting information stored in said first memory.

6. The system as recited in claim 5, wherein:
said third processor further outputs said second data input into said server out to said second medical image capture apparatus via said network, and
said second processor performs rewriting said first data into said second data input from said server in a case that it decides that contents of said second setting information included in said second data input from said server are not identical to those of said second setting information stored in said second memory.

7. The system as recited in claim 6, wherein:
said second processor appends, to said second data, identification information for identifying said second medical image capture apparatus in which said second data is stored, and outputs resulting data to said network, and
said first processor performs rewriting by referring to said identification information input via said network, and deciding that it is necessary to rewrite said second intrinsic information in said written second data input from said server, into said first intrinsic information in said backup data.

8. The system as recited in claim 5, wherein:
said second processor appends, to said second data, identification information for identifying said second medical image capture apparatus in which said second data is stored, and outputs resulting data to said network, and
said first processor performs rewriting by referring to said identification information input via said network, and deciding that it is necessary to rewrite said second intrinsic information in said written second data input from said server, into said first intrinsic information in said backup data.

9. The system as recited in claim 4, wherein:
said second processor appends, to said second data, identification information for identifying said second medical image capture apparatus in which said second data is stored, and outputs resulting data to said network, and
said first processor performs rewriting by referring to said identification information input via said network, and deciding that it is necessary to rewrite said second intrinsic information in said written second data input from said server, into said first intrinsic information in said backup data.

10. The system as recited in claim 4, wherein:
said server comprises a third processor,
said second processor appends, to said second data, identification information for identifying said second medical image capture apparatus in which said second data is stored, and outputs resulting data to said server via said network,
the third processor in said server outputs said second data along with said identification information to said first and second medical image capture apparatuses via said network,
in said first medical image capture apparatus, said first processor performs rewriting by referring to said identification information, and deciding that it is necessary to rewrite said second intrinsic information in said written second data input from said server, into said first intrinsic information in said backup data, and
in said second medical image capture apparatus to which said second data is input, said second processor performs restoration of said second data in said second memory using said second data input from said server.

11. The system as recited in claim 4, wherein:
said server comprises a third processor,
said second processor appends, to said second data, identification information for identifying said second medical image capture apparatus in which said second data is stored, and outputs resulting data to said server via said network, and
said third processor in said server refers to said identification information, and outputs said second data to said first medical image capture apparatus via said network, and
once said second data is input, said first processor performs rewriting into said second data.

12. The system as recited in claim 4, wherein: said server comprises third memory for storing therein said second data.

13. The system as recited in claim 3, wherein:
said second processor appends, to said second data, identification information for identifying said second medical image capture apparatus in which said second data is stored, and outputs resulting data to said network, and
said first processor performs rewriting by referring to said identification information input via said network, and deciding that it is necessary to rewrite said second intrinsic information in said written second data input from a server, into said first intrinsic information in said backup data.

14. The system as recited in claim 3, wherein: said second medical image capture apparatus comprises a second user interface for accepting an operator's input of said second setting information.

15. A method of controlling a medical image capture apparatus for capturing a medical image of an object to be imaged, said apparatus comprising memory and a processor, and being connected with another medical image capture apparatus via a network, wherein:
in said memory are stored: first data including first setting information set in said medical image capture apparatus, said first setting information including first intrinsic information intrinsic to said medical image capture apparatus, and first shared information shared with said other medical image capture apparatus; and backup data for said first intrinsic information, in said other medical image capture apparatus is stored second data including second setting information set in said other medical image capture apparatus, said second setting information including: second intrinsic information intrinsic to said other medical image capture apparatus and different from said first intrinsic information; and second shared information shared with said medical image capture apparatus, and the method comprising controlling, with said processor, to:

once said second data is input via said network, rewrite said first data stored in said memory into said second data, read said first intrinsic information in said backup data, and rewrite said second intrinsic information into which said first intrinsic information has been rewritten, into said first intrinsic information in said backup data.

16. The method of controlling the medical image capture apparatus as recited in claim 15, wherein:

said apparatus is connected to a server via said network, said server being connected with said other medical image capture apparatus via said network, and said second data input via said network is data that is input from said other medical image capture apparatus to said server via said network and stored there.

* * * * *